US 9,247,913 B2

(12) United States Patent
Flohr et al.

(10) Patent No.: US 9,247,913 B2
(45) Date of Patent: Feb. 2, 2016

(54) IDENTIFICATION OF POTENTIAL PERFUSION DEFECTS

(71) Applicants: Thomas Flohr, Uehlfeld (DE); Bernhard Schmidt, Fürth (DE)

(72) Inventors: Thomas Flohr, Uehlfeld (DE); Bernhard Schmidt, Fürth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 751 days.

(21) Appl. No.: 13/628,837

(22) Filed: Sep. 27, 2012

(65) Prior Publication Data

US 2013/0077845 A1  Mar. 28, 2013

(30) Foreign Application Priority Data

Sep. 28, 2011 (DE) .......... 10 2011 083 629

(51) Int. Cl.
*G06K 9/00* (2006.01)
*A61B 6/03* (2006.01)
*A61B 6/00* (2006.01)
*A61B 6/04* (2006.01)

(52) U.S. Cl.
CPC .............. *A61B 6/032* (2013.01); *A61B 6/4014* (2013.01); *A61B 6/463* (2013.01); *A61B 6/481* (2013.01); *A61B 6/482* (2013.01); *A61B 6/486* (2013.01); *A61B 6/503* (2013.01); *A61B 6/507* (2013.01); *A61B 6/5217* (2013.01); *A61B 6/0407* (2013.01); *A61B 6/0457* (2013.01); *A61B 6/5288* (2013.01); *A61B 6/541* (2013.01); *A61B 6/563* (2013.01)

(58) Field of Classification Search
None
See application file for complete search history.

(56) References Cited

U.S. PATENT DOCUMENTS

| 7,778,454 B2 | 8/2010 | Grasruck et al. |
| 2004/0101089 A1 | 5/2004 | Karau et al. |

(Continued)

FOREIGN PATENT DOCUMENTS

| CN | 1781456 A | 6/2006 |
| CN | 101028199 A | 9/2007 |

(Continued)

OTHER PUBLICATIONS

Priority Document German Application No. DE 102011083629.2 filed Sep. 28, 2011.
Chinese Office Action and English translation thereof dated May 6, 2014.

*Primary Examiner* — Vikkram Bali
(74) *Attorney, Agent, or Firm* — Harness, Dickey & Pierce, P.L.C.

(57) ABSTRACT

A method is disclosed for identifying potential perfusion defects in a tissue region through which blood flows in an object under investigation, based on at least one high-energy image data set covering the tissue region and at least one low-energy image data set covering the tissue region. A virtual contrast medium image data set is established based on the high-energy image data set and the low-energy image data set. Furthermore, first candidate perfusion regions within the virtual contrast medium image data set, and second candidate perfusion defect regions within a further image data set based on the high-energy image data set and/or the low-energy image data are detected, the first candidate perfusion defect regions being compared with the second candidate perfusion defect regions and, based on the comparison, potential perfusion defects being identified. Further disclosed are a corresponding image analysis apparatus and a computed tomography system.

21 Claims, 3 Drawing Sheets

(56) References Cited

U.S. PATENT DOCUMENTS

| | | |
|---|---|---|
| 2004/0153128 A1 | 8/2004 | Dalton |
| 2005/0018808 A1 | 1/2005 | Sabol |
| 2006/0122500 A1 | 6/2006 | Heismann et al. |
| 2007/0217570 A1 | 9/2007 | Grasruck et al. |
| 2010/0135564 A1 | 6/2010 | Bhotika |
| 2012/0245460 A1* | 9/2012 | Slomka et al. ............... 600/425 |
| 2014/0003688 A1* | 1/2014 | Hansis .......................... 382/130 |

FOREIGN PATENT DOCUMENTS

| | | |
|---|---|---|
| DE | 10355094 A1 | 6/2004 |
| DE | 102004055460 A1 | 4/2006 |
| DE | 102006009222 A1 | 9/2007 |
| DE | 102006009222 B4 | 2/2008 |

* cited by examiner

FIG 1

IDENTIFICATION OF POTENTIAL PERFUSION DEFECTS

PRIORITY STATEMENT

The present application hereby claims priority under 35 U.S.C. §119 to German patent application number DE 10 2011 083 629.2 filed Sep. 28, 2011, the entire contents of which are hereby incorporated herein by reference.

FIELD

At least one embodiment of the invention generally relates to a method for identification of potential perfusion defects in a defined tissue region, through which blood flows, in an object under investigation, based on at least one high-energy image data set covering said tissue region and at least one low-energy image data set covering the tissue region. A "perfusion defect" in this context is understood to be a partial region of tissue of an object under investigation through which, due to pathological causes, i.e. a malfunction, no, or insufficient, blood flows. At least one embodiment of the invention also generally relates to an image analysis apparatus for identifying potential perfusion defects, and/or a computed tomography system comprising an image analysis apparatus.

BACKGROUND

For many cardiological investigations, the spatially-resolved imaging of the blood supply to the myocardium by means of medical imaging techniques is an important tool for diagnostic back-up. A typical application example is the continuing checking of the effects of stenoses in the coronary arteries which, for example, have been identified previously in a cardiological computed tomography examination. In order to be able to estimate correctly the prognosis for the patient, it is helpful to investigate stenoses of this type with regard to their hemodynamic relevance. An answer needs to be found to the question of whether the blood supply through a stenosis is reduced at rest and/or under exertion and whether the myocardium is undersupplied or whether a still sufficient blood supply exists.

Normally, nowadays, such perfusion measurements to investigate the blood supply to the myocardium are carried out using magnetic resonance tomography methods ("MR perfusion investigations") or techniques of nuclear medicine, for example, SPECT. However, MR perfusion investigations are only available in specialist centers and are also very complex and costly. The imaging in nuclear medicine techniques such as SPECT suffers from low spatial resolution. They also often result in ambiguous or falsely positive findings. Alternatively, an assessment of the hemodynamic relevance of stenoses can be made through evaluation of the "Fractional Flow Reserve". Here, in the context of angiographic investigations by catheter, the pressure behind and in front of a stenosis are measured and, from these values, the pressure ratio (known as the Fractional Flow Reserve) is calculated. Investigations of this type have the disadvantage that they are invasive.

Computed tomography methods also essentially permit assessments to be made of the blood supply to the myocardium. For this purpose, the heart can be investigated with a conventional cardiac computed tomography protocol, for example, following injection of a, for example, iodine-containing contrast medium. A computed tomography protocol within the meaning of embodiments of the present invention should be understood to be a collection of control commands according to which the computed tomography system (hereinafter called "CT system") is controlled automatically during measurement, once started. Such protocols or measurement protocols are known to persons skilled in the art. In order to investigate the local blood supply to the myocardium, the CT values of the image pixels in the CT images of the myocardium can be evaluated, for example, by visual inspection or using suitable software methods.

In a healthy myocardium, it can be taken that the contrast medium is evenly distributed through the myocardium and therefore the CT values of all the image pixels of the myocardium are evenly elevated. Regions in the myocardium in which the image pixels have lower CT values than the surrounding myocardium can be interpreted as regions with reduced contrast medium uptake and therefore as zones of reduced blood supply, i.e. as having perfusion defects. Unfortunately, however, a local relative lowering in the CT values in the myocardium can also have other causes than a reduced contrast medium uptake, for example, a locally elevated fat content in the myocardium. Therefore with this investigation technique, a relative reduction in CT values for other reasons, cannot be distinguished from a genuine perfusion defect.

One possibility for solving this problem would be to perform the cardiac CT contrast medium recordings using a "dual-energy method". Here, the recordings of the tissue region of interest, that is, during a myocardial examination of the heart, are investigated with two different X-ray spectra, so that a CT raw data set is recorded with at least one first X-ray energy or with a first X-ray spectrum and a second CT raw data set is recorded with a second X-ray energy. A multi-energy method can also be used, in which yet further image data sets are recorded at still other energies. From the different CT raw data sets, a plurality of different image data sets which reproduce the CT values of the imaged tissue regions and of the contrast medium at the different X-ray spectra is reconstructed. Whereas fat and soft tissues have very similar CT values at different X-ray spectra, the CT value of most contrast media, particularly iodine, significantly increases with decreasing X-ray energy. Due to this strong change in the CT value with different X-ray spectra, it is possible to determine the contrast medium content per image pixel quantitatively and to reproduce this in a "virtual contrast medium" image. In a virtual contrast medium image data set, therefore, the contrast medium content of each individual image pixel in the myocardium can be given quantitatively as a measure for the local blood supply. In this way, regions in the myocardium in which less contrast medium has been taken up due to a perfusion defect, can be readily identified with high sensitivity. However, evaluation of the images following such a method is relatively severely laden with artifacts. Due to often unavoidably high contrast medium concentrations, for example, in the right ventricle of the heart, artifacts arise in a contrast medium image data set of this type which can mimic a locally reduced iodine concentration in the myocardium and can therefore simulate a perfusion defect. Due to other inconsistencies between the CT images recorded with different X-ray spectra, for example, beam-hardening, pixel artifacts can arise during calculation of the contrast medium content which, as sites of darkening in the myocardium, mimic perfusion defects in the myocardium.

SUMMARY

An embodiment of the present invention provides an improved method and/or an improved image analysis apparatus for identifying potential perfusion defects.

An embodiment is directed to a method for the identification of potential perfusion defects (PD) in a defined tissue region (M) through which blood flows in an object under investigation (P), based on at least one high-energy image data set (HEB) covering said tissue region and at least one low-energy image data set (NEB) covering the tissue region, comprising the following steps:

establishment of a virtual contrast medium image data set (KB) based on the high-energy image data set (HEB) and the low-energy image data set (NEB), detection of first candidate perfusion defect regions (KKP) within the virtual contrast medium image data set (KB), detection of second candidate perfusion defect regions (MKP) within a further image data set (MB) based on the high-energy image data set (HEB) and the low-energy image data set (NEB), and comparison of the first candidate perfusion defect regions (KKP) with the second candidate perfusion defect regions (MKP) and identification of potential perfusion defects (PD) based on the comparison.

An embodiment is directed to an image analysis apparatus (30) for identifying potential perfusion defects (PD) in a defined tissue region (M) through which blood flows in an object under investigation (P), comprising the following components:

an image data set interface (31) for reading in at least one high-energy image data set (HEB) covering the tissue region (M) of the object under investigation (P) and at least one low-energy image data set (NEB) covering the tissue region (M) of the object under investigation (P), a contrast medium image determination unit (32) which is designed to determine a virtual contrast medium image data set (KB) based on the high-energy image data set (HEB) and the low-energy image data set (NEB), a perfusion defect identification unit (34) which is designed in order to detect first candidate perfusion defect regions (KKP) within the virtual contrast medium image data set (KB), detect second candidate perfusion defect regions (MKP) within a further image data set (MB) based on the high-energy image data set (HEB) and/or the low-energy image data set (NEB), and identify potential perfusion defects (PD), based on a comparison of the first candidate perfusion defect regions (KKP) with the second candidate perfusion defect regions (MKP).

An embodiment is directed to a computed tomography system comprises an image analysis device.

An embodiment is directed to a computer program product which can be loaded directly into a memory unit of an image analysis apparatus, and comprises program code sections, in order to carry out all the steps of the method when the program is executed in the image analysis apparatus.

BRIEF DESCRIPTION OF THE DRAWINGS

The invention will now be described again in greater detail on the basis of example embodiments and making reference to the attached drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The method according to an embodiment of the invention for identifying potential perfusion defects in a defined tissue region, through which blood flows, of an object under investigation based on a high-energy image data set covering said tissue region, i.e. reproducing the tissue region in the image data, and a low-energy image data set covering the tissue region, comprises at least the following steps:

A virtual contrast medium image data set is established based on the high-energy image data set and the low-energy image data set. The creation of a virtual contrast medium image data set can be achieved with a conventional method, for example, one of the methods disclosed in DE 10 2006 009 222 B4, the entire contents of which are hereby incorporated herein by reference.

Within the virtual contrast medium image data set, first candidate perfusion defect regions are detected.

Furthermore, second candidate perfusion defect regions are detected within a further image data set based on the high-energy image data set and the low-energy image data set. The further image data set may be, for example, the high-energy image data set or the low-energy image data set themselves. Preferably, said data set is a mixed image created, for example, by pixel-wise weighted addition or subtraction from the high-energy image data set and the low-energy image data set.

In the context of at least one embodiment of the invention, an image data set is, for example, a layer stack of a plurality of images covering a particular volume, for example, a complete heart muscle or an interesting portion of the heart muscle. In place of a layer stack, said data set can naturally also be a volume data set, for example, a single 3-D image file, in which a CT value is stored for each voxel at a specific time point. The data set may be an image data set or a time-dependent image data set, for example, a two-dimensional series of images of the same layer, which shows the change of the layer over time, or a four-dimensional image data set which, for example, covers the change over time of a complete volume, for example, again in the form of a plurality of layer stacks.

Furthermore, in the context of at least one embodiment of the invention, a comparison is made between the first candidate perfusion defect regions and the second candidate perfusion defect regions and determination, i.e. identification of potential perfusion defects is made based on this comparison. In other words, the candidate perfusion defects in the two different images, specifically, firstly, the contrast medium image data set and, secondly, the further image data set, are correlated to one another and this correlation result is utilized to identify the potential perfusion defects.

In this way, it is possible to combine synergistically the advantages of detecting possible perfusion defects in a contrast medium image data set and the advantages of the detection of perfusion defects in a "normal" single-energy CT image data set, as would be recorded at only one energy, and thus to overcome the advantages of both methods. The result can thus be significantly improved, since false positive findings can be prevented with significantly greater reliability. However, a method of this type is associated with only slightly increased complexity compared with simple evaluation of a dual-energy method. Additional image recordings, and the associated increased exposure of the patient, are therefore not necessary.

It should be noted at this point that the steps do not have to be carried out in the sequence given above, one after the other, or separately. It is, for example, entirely possible, after creation of the contrast medium image data set, for the detection of the first candidate perfusion defect regions and/or of the second candidate perfusion defect regions to be carried out in a different sequence or simultaneously. Similarly, comparison of the candidate perfusion defect regions and the determination, based thereon, of potential perfusion defects can be carried out simultaneously with detection of the candidate perfusion defect regions within the virtual contrast medium image data set and/or within the further image data set.

As will be described below, depending on the precise configuration of the method, it is preferably possible to carry out the determination of the potential perfusion defects in the image data sets fully automatically, so that, for example, at the end of the process, the potential perfusion defects are displayed to a user, for example a physician, in an image data set and said user can then merely accept or, more precisely, interpret or reject said defects. Semi-automatic methods are also conceivable, wherein an operator can be supported in the detection of the candidate perfusion defect regions and in the comparison by way of a suitably designed image analysis apparatus.

An image analysis apparatus according to at least one embodiment of the invention for performing a method of this type requires at least the following components:

An image data set interface for reading in at least one high-energy image data set covering the tissue region of the object under examination and at least one low-energy image data set covering the tissue region of the object under investigation. This high-energy image data set and this low-energy image data set can be generated in advance at an arbitrary time point by means of X-ray measurements, preferably computed tomography measurements, at different X-ray energies following the administration of a contrast medium. In such measurements, an "X-ray energy" is usually given with a defined value, for example, by means of the X-ray tube voltage (i.e. the acceleration voltage for the electrons), even if an X-ray energy does not have a discrete value but, as is natural, always comprises an energy spectrum with a particular bandwidth about the given value. Typical X-ray energies for a computed tomography dual-energy measurement are about 80 keV for the low-energy image data set and 140 keV for the high-energy image data set.

Furthermore, the image analysis apparatus requires a contrast medium image determination unit which is designed to determine a virtual contrast medium image data set based on the high-energy image data set and the low-energy image data set. The image analysis apparatus must also have a perfusion defect identification unit which is designed to detect first candidate perfusion defect regions within the virtual contrast medium image data set, and to detect second candidate perfusion defect regions within a further image data set based on the high-energy image data set and/or the low-energy image data set and to identify potential perfusion defects, based on a comparison of the first candidate perfusion defect regions with the second candidate perfusion defect regions.

Insofar as the further image data set is a mixed image from the high-energy image data set and the low-energy image data set, the image analysis apparatus advantageously has a corresponding mixed image determination unit designed to determine a mixed image based on the high-energy image data set and the low-energy image data set. A mixed image of this type can, for example, be calculated so as to correspond to a normal single energy CT image data set recorded, for example, at a typical X-ray energy of 120 keV. This has the advantage that, for the analysis of the image data set, for example, for later segmentation, already existing analysis software components that are usually matched to such X-ray energies can be, at least partially, made use of.

An image analysis apparatus of this type can be part of a computed tomography system, that is, the apparatus can be installed, for example, on a control or evaluating computer of the computed tomography system. An embodiment of the invention therefore also includes a computed tomography system, preferably a dual-source computed tomography system or a multi-source computed tomography system with an image analysis apparatus of this type. An image analysis apparatus of this type can essentially also be realized on an independent computer unit, such as a pure evaluating unit of a radiological network or the like which, for example, is linked to a computed tomography system for data transfer or can be supplied with suitable data by other means.

In particular, the contrast medium image determination unit and the perfusion defect identification unit can each be realized as software modules on a suitable computer with suitable memory possibilities. The image data set interface can also be realized in the form of pure software, provided only the acceptance of the high-energy and low-energy image data sets from other program units is required. However, the image data set interface can essentially also be realized as a combined hardware and software interface, in order to realize the external acceptance by other devices. An embodiment of the invention therefore also includes a computer program product which can be loaded directly into a memory unit of an image analysis apparatus of this type, with program code segments in order to carry out all the steps of the method according to an embodiment of the invention. A software-based realization of this type has the advantage that already existing image analysis apparatuses used for analysis of corresponding image data (for example, suitable control apparatus of computed tomography systems) can be modified by implementation of the program in a suitable way, in order to function in accordance with the method according to an embodiment of the invention.

The dependent claims and the further description contain particularly advantageous embodiments and developments of the invention. In particular, the claims of one category can be developed similarly to the claims of another category.

Preferably, in the context of the method, a partial region of the tissue region to be investigated can only be identified as a potential perfusion defect if said partial region is detected as a candidate perfusion defect region both in the virtual contrast medium image data set and in the further image data set. In this way, the false positive findings for the occurrence of which there is a high level of risk in the initially mentioned method can be prevented relatively reliably. In regions where, for example, the contrast medium image data set suggests a reduced contrast medium uptake, but the relative CT values of the further image data set, which corresponds to an image data set recorded with a single energy technique, are not reduced, it can be assumed with a high probability that such regions are artifacts which have been evoked by the dual-energy evaluation. Conversely, in regions in which reduced CT values of the further image relative to the surroundings suggest a perfusion defect, but the contrast medium images do not show a reduced contrast medium uptake, it can be assumed with a high probability that said regions are other tissue changes in the myocardium, for example, local fat deposits. Since, in the virtual contrast medium image data set, the actual contrast medium content per image point (pixel or voxel) is shown, the contrast medium image data set is not sensitive to changes in the tissue composition of the myocardium, for example, a raised fat content. This means that, perfusion defects cannot be mimicked in the contrast medium image data set due to an increased fat content.

It is particularly advantageous in this context if the detection of the first candidate perfusion defect regions within the virtual contrast medium image data set and the detection of the second candidate perfusion defect regions within the further image data set take place completely independently of one another, that is, not influenced by one another. It may also be possible, however, in order to accelerate the method, that the first candidate perfusion defect regions are determined only in the virtual contrast medium image data set and that said regions are then used to search in the further image data set specifically at the relevant sites for second candidate perfusion defect regions, or conversely, to determine only the second candidate perfusion defect regions in the further image data set and then, on the basis of these regions, to search for the first candidate perfusion defect regions within the virtual contrast medium image data set.

The detection of the candidate perfusion defect regions can be carried out visually in the respective image data sets, in that the image data sets are displayed to the user on an output device. Preferably, however, the detection of the first candidate perfusion defect regions within the virtual contrast medium image data set and/or the detection of the second candidate perfusion defect regions within the second image data set is carried out automatically.

For this purpose, it is preferable for the image points which could be attributed to a potential perfusion defect or a candidate perfusion defect to be identified with the aid of a threshold value analysis. For example, for the contrast medium image data set, a particular contrast medium value can be set as the threshold value and, if the contrast medium value is undershot at a particular pixel or voxel, the latter is determined to be insufficiently perfused and therefore as belonging to a potential perfusion defect. Preferably, further aspects can be taken into account herein, for example, that a plurality of such image points must lie adjoining one another with values below the threshold in order for a possible perfusion defect to be brought into consideration. In a similar way, a threshold value or limit value can be set for the further image data set. If the CT value is below this threshold value, then the corresponding pixel is also considered here as a possible pixel of a potential perfusion defect or candidate perfusion defect region.

For a later comparison of the candidate perfusion defect regions, said regions can be segmented in advance within the respective images. Suitable segmentation methods for "cutting out" or otherwise isolating particular regions from the image data sets, for example, region growing methods, etc., are known to persons skilled in the art. For this purpose, the image analysis apparatus should preferably have a suitable segmentation unit, for example, in the form of a software module.

For comparison, image data of the virtual contrast medium image data set and corresponding image data of the further image data set are output simultaneously, preferably overlaid on one another, to a display device, i.e. imaged. Such a simultaneous display of the image data is possible—as in an automatic comparison or automatic correlation—in the method according to an embodiment of the invention without complex additional registration of the image data sets, since both the virtual contrast medium image data set and also the further image data set are based on the same high-energy image data set and low-energy image data set. Only on creation of the virtual contrast medium image data set or on creation of the further image data set must the high-energy image data set and the low-energy image data set possibly be registered onto one another in a suitable manner depending on the means of creation of the data sets. However, suitable methods are sufficiently well known to persons skilled in the art.

When overlaying or parallel display is performed, the complete data sets or partial image data sets may be involved in each case, provided they cover candidate perfusion defect regions or even only the already detected candidate perfusion defect regions. By way of simultaneous visual imaging of this type, in particular overlaying, a visual comparison and therefore identification of potential perfusion defects as well as verification or rejection of already automatically identified perfusion defects is readily achievable.

Automatic determination of perfusion defects based on previously automatically determined first and second candidate perfusion defect regions is possible, for example, in that the candidate perfusion defect regions determined are marked in the image data sets and the image data sets are then automatically (virtually) overlaid and the marked regions are investigated for matching markings. The match may be evaluated, for example, depending on how many pixels are marked in a particular coherent region in both image data sets. The markings can also be coupled, for example, with suitable numerical values and, in the context of identifying the perfusion defects, the numerical values of the individual pixels are added up and compared again with a threshold value. Pixels which then lie above said threshold value are analyzed for a potential perfusion defect with regard to further criteria in the surroundings. If, for example, there is a sufficient number of mutually associated pixels lying above the threshold value, said pixels have then to be attributed to a potential perfusion defect.

In an alternative method, for example, only the candidate perfusion defect regions in one of the image data sets are detected in advance and automatically segmented and then the segmented regions overlaid onto the other image data set, so that the determination of the further candidate perfusion defect regions and a comparison of the candidate perfusion defect regions and the identification of the potential perfusion defects can possibly be carried out in one procedure.

Preferably, in the overlaid output, previously detected first candidate perfusion defect regions and/or previously detected second candidate perfusion defect regions are again marked in a suitable manner, i.e. imaged differently from the surrounding tissue, preferably with a suitable color coding. Marking of this type is possible independently of whether the image data sets altogether are overlaid or whether, for example, only already segmented regions are overlaid on another image data set.

The method is particularly suitable for identifying perfusion defects in the myocardium, i.e. the defined tissue region is preferably a myocardial tissue region. As described above, particularly in this region, special problems occur, so that the method can be particularly usefully applied there. However, embodiments of the invention are not fundamentally restricted to use in myocardial investigations, but rather tissues in all regions of the body where a reduced contrast medium concentration in the contrast medium image can be identified as a reduced local blood volume.

The measurements can be made both at rest and under exertion, for example, called forth by the administration of adenosine or the like. In this way, therefore, irreversible perfusion defects which are present at rest and under exertion, as well as reversible perfusion defects, which arise only under exertion, can be detected.

In a preferred variant, the measurement is made at a time point following a contrast medium administration in that the coronary arteries are particularly well contrasted and thus also the myocardium has a slightly raised CT value due to the contrast medium. Investigations of this type are designated "First-Pass Enhancement" investigations. This is possible in that, for example, following automatic injection of the contrast medium, the heart is investigated with a normal heart CT dual-energy protocol in which, for example, an ECG-triggered sequential protocol or an ECG-gated spiral protocol is used. The investigation is controlled by analysis of a test bolus or by way of typical bolus-trigger methods such that the start takes place, as precisely as possible, at the first-pass enhancement time point. Alternatively or additionally, it is also possible to evaluate the late-enhancement, wherein there is a wait of several minutes after an injection of the contrast medium before recording of the CT images.

In principle, in order to carry out the method according to at least one embodiment of the invention, a low-energy image data set and a high-energy image data set which were measured at an arbitrary time point previously in a computer tomograph can be accepted. Equally, a previously measured low-energy projection data set and a high-energy projection data set can be accepted and reconstructed in the context of the method according to at least one embodiment of the invention. The acceptance of data can be carried out, for example, via a network.

In one variant, however, the method according to at least one embodiment of the invention includes the recordings of the high-energy image data set covering the tissue region of the object under investigation and of the low-energy image data set covering the tissue region of the object under investigation by way of X-ray measurement with different X-ray energies following administration of contrast medium to the object under investigation. That is, the complete method is started with the measurement and thereafter the identification of potential perfusion defects in the defined tissue region under investigation is carried out on the basis of measurement data and/or the image data reconstructed therefrom, for example, on a control apparatus of the computer tomograph.

The measurements at different energies are favorably made at a short temporal separation, so that no significant movements of the object under investigation or at least the part of the object under investigation to be recorded, take place between the high-energy image data set and the low-energy image data set. A short temporal separation should be understood to mean a time period in which the contrast medium concentration in the object under investigation changes by a maximum of 5%. For the recording of the high-energy image data set and of the low-energy image data set, in principle, any computed tomography system can be used. A short duration between the measurement of the high-energy image data set and the low-energy image data set can be ensured if, for example, a computed tomography system has a detector width in the advance direction which covers the whole defined tissue region, i.e. the whole of the heart.

Particularly preferably, however, the recording of the raw data sets (projection data sets) necessary for reconstruction of the high-energy image data set and the low-energy image data set is carried out in a dual-source computer tomograph with at least two X-ray sources, the X-ray sources simultaneously emitting X-rays of different energies. The X-ray sources are usually arranged together at the gantry offset by 90° to one another and rotatable about the tomograph longitudinal axis, a first of the X-ray sources emitting X-rays of a first X-ray energy and a second of the X-ray sources emitting X-rays of a second X-ray energy different from the first X-ray energy. As a result, following the reconstruction, a high-energy image data set and a low-energy image data set exist, differences due to movement of the object under investigation being almost excluded, since the registration of the image data sets to one another is automatically provided by the measuring process and is perfect. In principle, as mentioned above, the use of more than two X-ray sources is also possible.

In the following examples, it is assumed that potential perfusion defects are to be identified within the myocardium of a patient. However, this does not preclude the possibility of identifying perfusion defects in other tissues as well.

Figure 1:
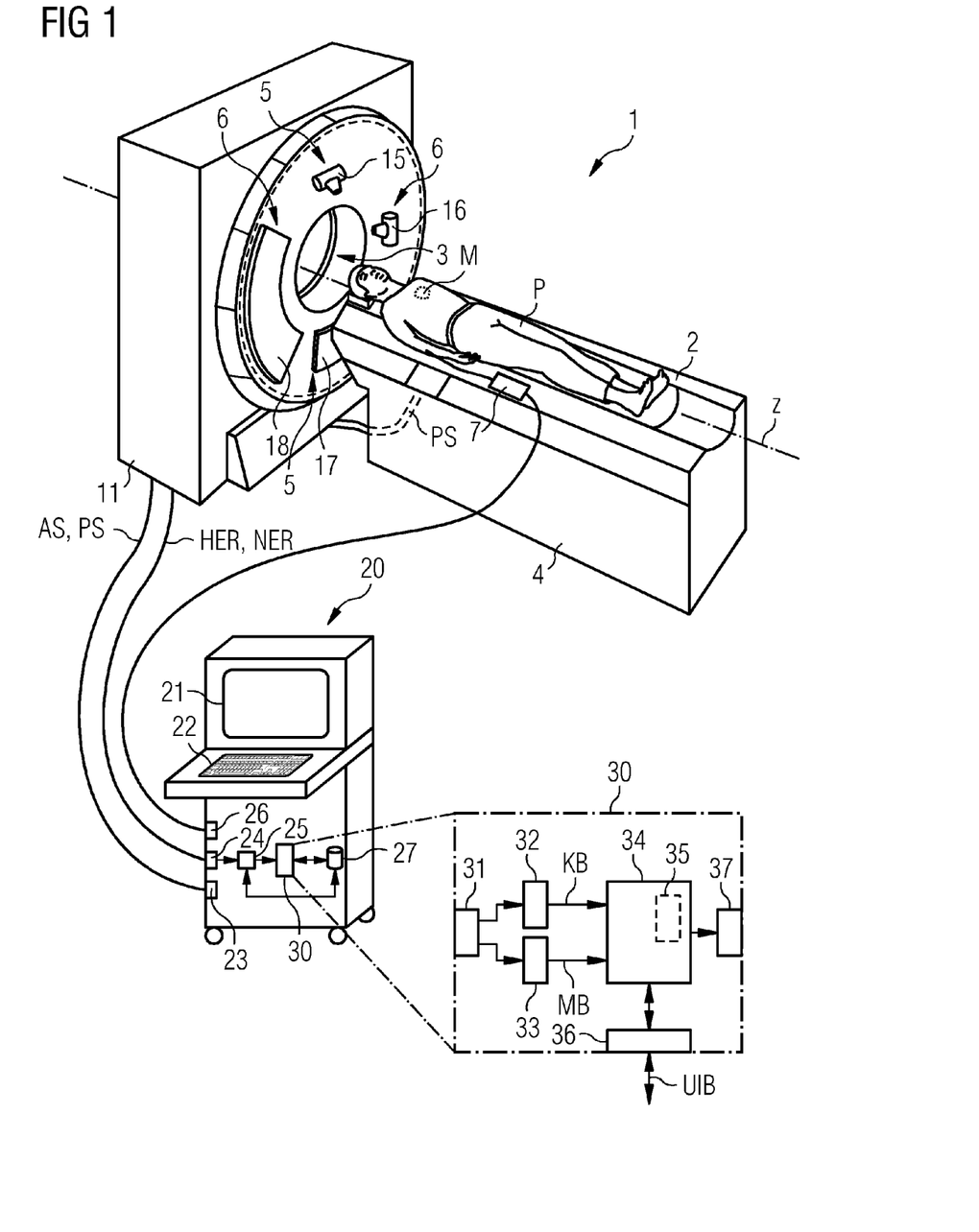
FIG. 1 is a schematic representation of an example embodiment of a computed tomography system according to the invention.

Shown schematically in FIG. 1 is a computed tomography system (CT system) 1 with an image analysis apparatus 30.

The CT system 1 essentially includes a conventional dual-source scanner 11, in which two data acquisition systems 5, 6, each having an X-ray source 15, 16 and a detector 17, 18 lying opposing the X-ray source 15, 16 and arranged on a gantry 10, rotate round a measurement space 3. Arranged in front of the scanner 11 is a patient support device or patient table 4, the upper part of which 2 with an object under investigation P, here a patient, positioned thereon can be displaced relative to the scanner 11 along the z-direction, which corresponds to the system axis z, through the measurement space 3, in order to move the patient P through the measurement space 3 relative to the data acquisition systems 5, 6. The scanner 11 and the patient table 4 are controlled by a control device 20, from which, via a conventional control interface 23, control data PS come for table positioning and control data AS for the data acquisition systems 5, 6 in order to control the CT system 1 according to pre-defined measurement protocols in conventional manner.

It is fundamentally possible to move the patient along the z-axis and simultaneously to cause the X-ray sources 15, 16 to circulate, so that a helical path is followed by each X-ray source 15, 16 relative to the patient P during the measurement. In this way, volume data from the body of the patient are recorded. In another, sequential measurement method, the patient P is moved forward step-wise in the z-direction and, while the table is standing still, the X-ray sources 15, 16 each circulate round at least a particular angular periphery (in general, at least 180°) in order to generate sufficient projections in a particular sectional image plane. In this variant, therefore, volume data in the form of layer stacks with individual layer images perpendicular to the system axis z are generated. In the context of the invention, all these methods are usable. In the case of the dual-source scanner 11 described, both the X-ray sources 15, 16 are adjusted to function with different X-ray tube voltages and thus to emit X-rays of different energies. In this way, two projection data sets (hereinafter called "raw data sets") are generated simultaneously during a measurement, specifically a low-energy raw data set NER and a high-energy raw data set HER.

It should be noted that, in place of the system shown in FIG. 1, any other computed tomography system can be used, in order to generate raw data sets NER, HER for the method according to an embodiment of the invention. Firstly, it is possible to use scanners with only one data acquisition system and in two closely successive measurements, to set the X-ray tube voltage differently. The scanner can also be designed differently and, for example, in place of a detector moving together with the X-ray tube, on the opposite side therefrom, can have a circular detector ring, the detector elements of which are read out to follow the circulating X-ray source. Other design variants are also conceivable.

The raw data sets NER, HER acquired by way of the data acquisition systems 5, 6 are then passed to the control device 20 via a raw data interface 24. In a reconstruction unit 25, a low-energy image data set NEB is reconstructed from the low-energy raw data set NER and a high-energy image data set HEB is reconstructed from the high-energy raw data set HER. The reconstruction of the image data sets from the raw data sets can be carried out with any desired method. Numerous reconstruction methods, for example, filtered back-projection methods, iterative reconstruction methods, etc., are known to persons skilled in the art.

In order to be able to generate automatically controlled contrast medium images of the tissue region of interest M, in this case the myocardium M, of the patient P, a contrast medium pump 7 can be controlled by the control device 20 via a contrast medium pump interface 26. With this contrast medium pump 7, a precisely dosed quantity of contrast medium can then be administered to the patient via a previously placed access point.

The control device 20 in this case is also equipped with an image analysis apparatus 30 according to an embodiment of the invention, which is shown again enlarged in FIG. 1, together with the components thereof.

The image analysis apparatus 30 has an image data set interface 31 for adopting the image data sets HEB, NEB generated by the reconstruction unit 25. The image data sets HEB, NEB generated by the reconstruction unit 25 can initially be stored directly in a memory unit 27 and then accepted therefrom. The reconstruction unit 25 can also output the reconstructed image data sets directly via a suitable output interface, for example, to the screen 21.

Furthermore, the image analysis apparatus 30 has a contrast medium image generating unit 32, which generates a virtual contrast medium image data set KB from the high-energy image data set HEB and the low-energy image data set NEB accepted from the image data set interface 31 in conventional manner. The image analysis apparatus 30 also comprises a mixed image computation unit 33 which generates a mixed image data set MB from the high-energy image data set HEB and the low-energy image data set NEB by weighted addition. Both the virtual contrast medium image data set KB and the mixed image data set MB are taken up by a perfusion defect identification unit 34 which identifies the potential perfusion defects, as will later be described making reference to FIGS. 2 and 3. A segmentation unit 35 can also be a component part of this perfusion defect identification unit 34, in order to segment candidate perfusion defect regions found in the image data sets. Said perfusion defect identification unit 34 is also connected via a driver interface 36 to a user interface, for example, a display device 21 and/or a keyboard 22 of the control device 20 or to other user interfaces, for example, a mouse or the like. User interface commands UIB can be transferred between the user interfaces, i.e. the keyboard, a graphical user interface on the display device 21 with a mouse or other pointing device, etc., by means of said driver interface 36, to the perfusion defect identification unit 34 and, conversely, user interface commands UIB of this type can be output from the perfusion defect identification unit 34, in order, for example, to output images in a particular way on the display device 21, in particular also to request user input within a menu, etc.

By way of a network interface and a memory interface 37, the image analysis apparatus 30 is linked to a memory unit 27 of the control device 20, for intermediate storage of data or to store finished image data with, for example, potential perfusion defects marked therein, or simply to allocate corresponding data on potential perfusion defects to images already stored in the memory unit 27.

Normally, the control device 20 is connected via a suitable interface to a network, for example, a radiological information system and/or a PACS (Picture Archiving and Communication System), in order, for example, to transfer raw data sets and/or image data sets to other computer units, for example, assessment stations, by way of printers or other output devices and in order to place data in long-term archiving. Similarly, data can be accepted via such interfaces.

At least the reconstruction unit 25 and the image analysis apparatus 30 with the different components thereof are embodied here in the form of software on a processor or a plurality of cooperating processors of the control device 20. However, it should be noted that different possible variations of the configuration of the control device 20 are possible. Thus, as will presumably often be the case, the raw data interface 25 and the reconstruction unit 23 are independent here, that is, are not realized in the control device 20 as part of the image analysis apparatus 30 according to an embodiment of the invention and the image analysis apparatus 21 accepts from the independent reconstruction unit 25 the necessary image data sets HEB, NEB. It is essentially also possible for the reconstruction unit 25 to be realized as part of the image analysis apparatus 30 and, in place of an image data set interface 31, for the image analysis apparatus 30 accordingly to have a raw data interface.

Possible modes of operation of the image analysis apparatus 30 will now be described in greater detail making reference to FIGS. 2 and 3.

Figure 2:
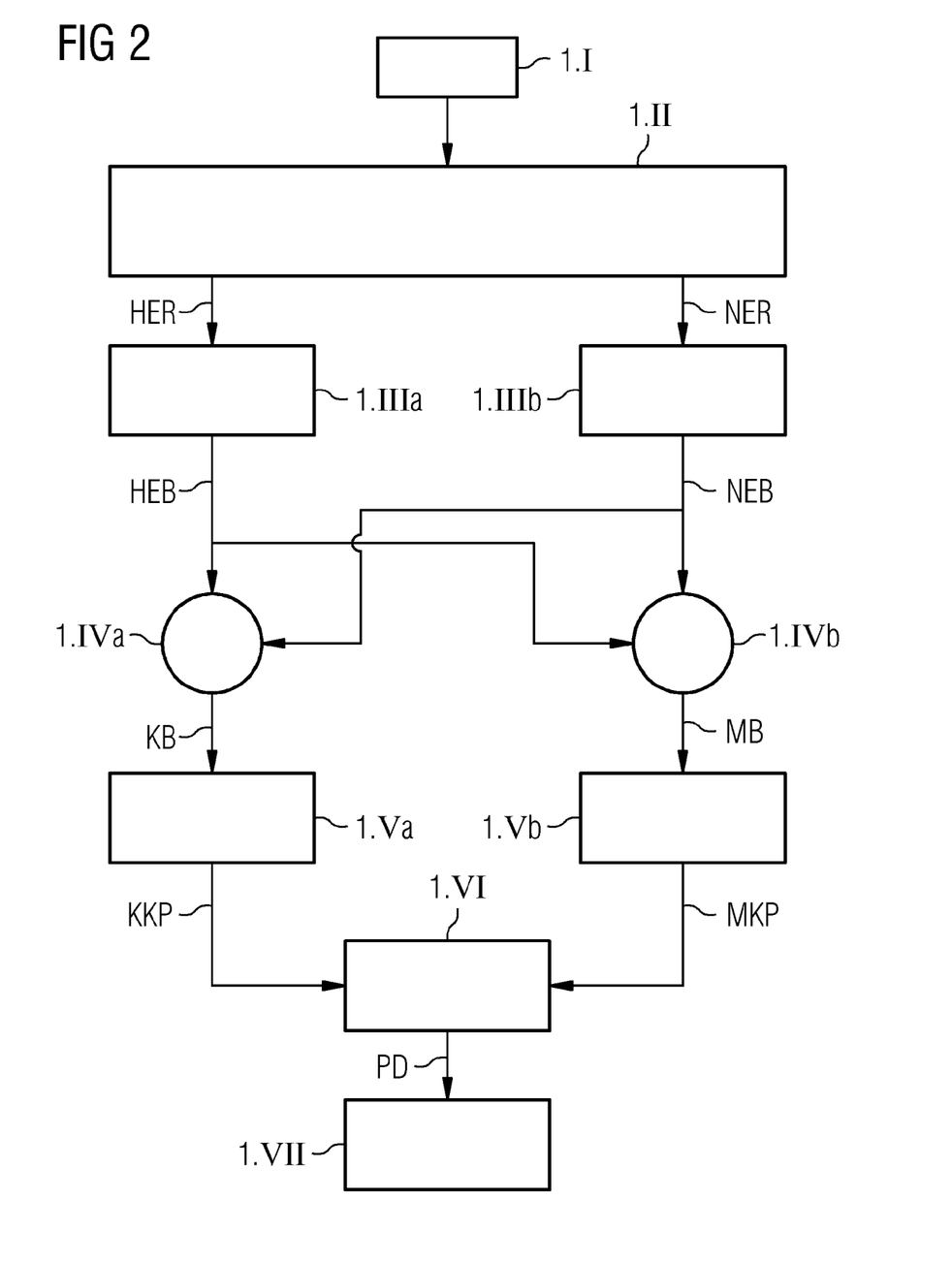
FIG. 2 is a flow diagram of a possible first example embodiment of the method according to the invention.

FIG. 2 shows a first variant of the method according to an embodiment of the invention, which operates fully automatically and, at the end, outputs an image data set to an operator with the potential perfusion defects marked therein, so that based on the suggestions, the operator can confirm and further evaluate or reject the potential perfusion defects PD, or based on the proposed potential perfusion defects, can create an assessment with a complete diagnosis.

Before the start of the actual imaging process or the evaluating procedure according to an embodiment of the invention, initially in step I, it is provided that a contrast medium is administered to the patient in a suitable manner. In step 1.II, a dual-energy scan is then carried out, a dual-energy CT system preferably being used in order to determine the high-energy raw data HER and the low-energy raw data NER simultaneously. The different X-ray energies can be, for example, 140 keV for the high-energy raw data set HER and 80 keV or 100 keV for the low-energy raw data set NER. In order to carry out a first-pass enhancement measurement at the right time point, the recording process can be controlled by way of a test bolus or by conventional bolus-trigger methods.

The result of this dual-energy measurement is, firstly, a high-energy raw data set HER and, secondly, a low-energy raw data set NER. In step 1.IIIa, a high-energy image data set HEB is reconstructed based on the high-energy raw data set HER. Before this, simultaneously or thereafter, in step 1.IIIb, a low-energy image data set NEB can be generated from the low-energy raw data set NER.

Then, in a step 1.IVa, from the high-energy image data set HEB and the low-energy image data set NEB, a virtual contrast medium image is created. Since in most cases, iodine-containing preparations are used as the contrast medium, this image is often known as the "iodine image". Before this, in parallel or later, in step 1.IVb, a mixed image data set MB, preferably a mixed image data set which would correspond to a single-energy measurement at a tube voltage of approximately 120 keV is created from the high-energy image data set and the low-energy image data set by image point-wise (i.e. pixel-wise or voxel-wise) weighted addition.

In step 1.Va, at an arbitrary time point after creation of the contrast medium image data set KB, first candidate perfusion defect regions KKP are detected in this contrast medium image data set KB. For this purpose, for example, a threshold value method can be used wherein for each pixel, it is tested whether the contrast medium value is sufficient, i.e. lies above the threshold value or not. Insofar as, in a particular environment, a plurality of pixels have too low a contrast medium value, this region is detected as a first candidate perfusion defect region KKP. In a similar manner, in step I.Vb, second candidate perfusion defect regions MKP are detected in the mixed image data set MB at an arbitrary time point after creation of the mixed image data set MB. This can also be performed with a threshold value method, in that the pixels are tested as to whether the CT value lies above a threshold value or not.

In step 1.VI, a correlation or comparison of the first candidate perfusion defect regions KKP and the second candidate perfusion defect regions MKP is then performed. For this purpose, for example, in a particularly simple variant, the contrast medium image data set KB and the mixed image data set MB, in each of which the pixels belonging to the candidate perfusion defect regions KKP, MKP are emphasized in suitable manner, for example, by particularly high numerical values, can be simply overlaid or added. With a further threshold value, it can then be determined at which pixels both a candidate perfusion defect region KKP in the contrast medium image data set KB and a candidate perfusion defect region MKP in the mixed image data set MB was determined. The potential perfusion defects PD thereby determined can then be output in step 1.VII in a suitable manner, for example, in that the mixed image data set MB is displayed on a screen and the potential perfusion defects PD in the mixed images are highlighted in a suitable manner, for example, by color-coding.

Figure 3:
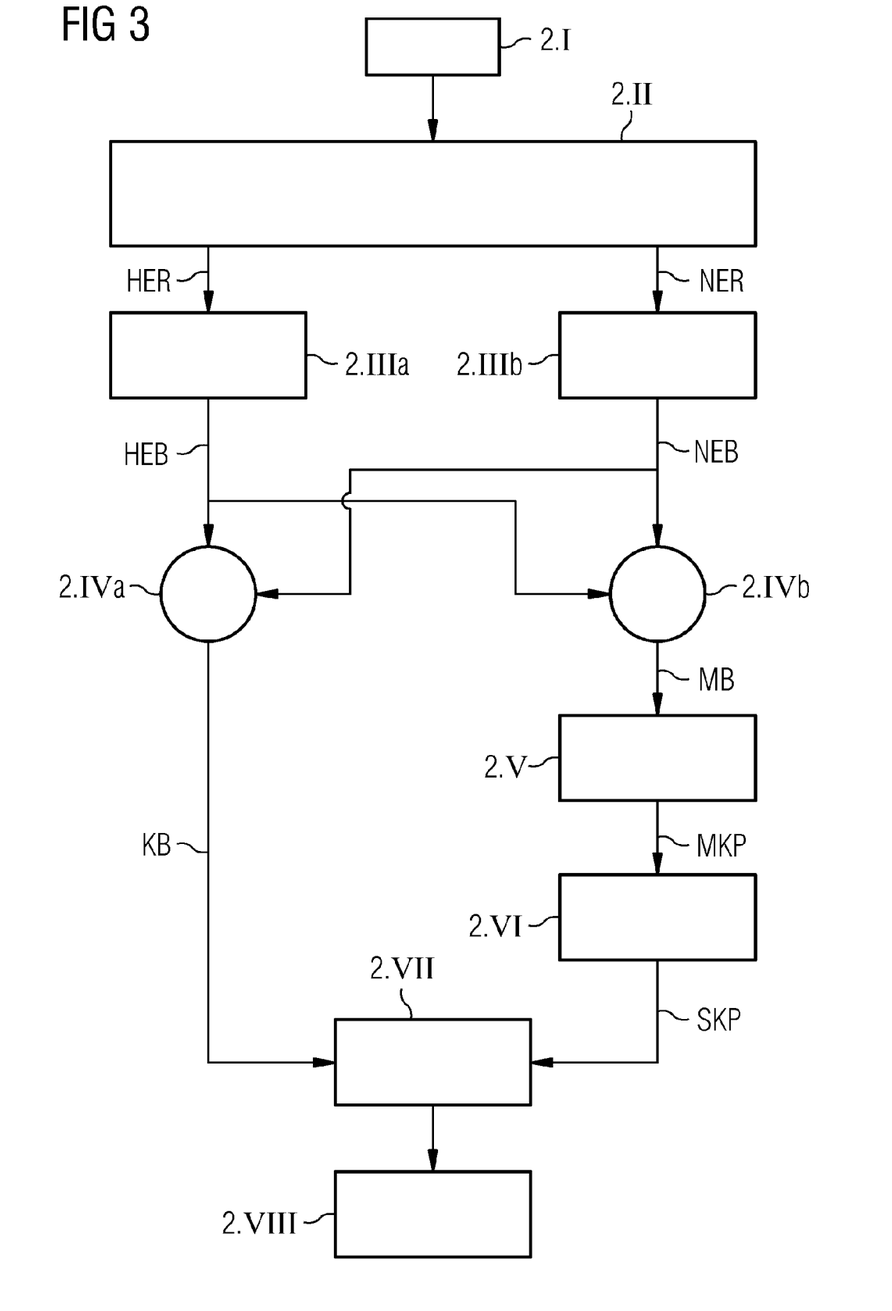
FIG. 3 is a flow diagram of a possible second example embodiment of the method according to the invention.

FIG. 3 shows a method variant which operates semi-automatically, that is, with the intervention of an operator. Here also, in step 2.I, before the start of the actual imaging method or of the evaluating method according to an embodiment of the invention, a contrast medium is administered. In step 2.II, a dual-energy CT scan is carried out in similar manner to the method according to FIG. 1, so that subsequently, from a high-energy raw data set HER, in step 2.IIIa, a high-energy image data set HEB and, from a low-energy raw data set NER, in step 2.IIIb, a low-energy image data set NEB can be reconstructed.

Furthermore, in the method according to FIG. 3, as in the method according to FIG. 2, in step 2.VIa, from the high-energy image data set HEB and the low-energy image data set NEB, a virtual contrast medium image data set KB is generated, and in step 2.IVb, from the high-energy image data set HEB and the low-energy image data set NEB, a mixed image data set MB is generated. However, subsequently it is only in step 2.V in the mixed image data set MB that automatic detection of candidate perfusion defect regions MKP takes place. This can be performed in the same way as in step 1.Vb of the method according to FIG. 2.

Then in step 2.VI, segmentation of the detected candidate perfusion defect regions MKP in the mixed image data set MB is performed. These segmented perfusion defect regions SKP comprise only the image data for the regions of the tissue which, according to the detection in step 2.V, could possibly be attributed to a perfusion defect. Then, in step 2.VII, said segmented regions SKP are displayed on an indicator overlaid on the virtual contrast medium image data set KB, so that the candidate perfusion defect regions MKP detected in the mixed image data set MB are marked within the contrast medium image data set KB. The operator now has the possibility of analyzing the contrast medium image data set KB visually in order to find candidate perfusion defect regions KKP in the contrast medium image data set KB, and can simultaneously determine whether said defect regions correlate to the automatically found candidate perfusion defect regions MKP of the mixed image data set MB. This takes place in step 2.VIII. At the same time, the operator can determine directly the potential perfusion defect regions PD and immediately verify said regions and, if desired, undertake further assessment or reach a final diagnosis, based on the correlation, or the overlaid imaging, of the segmented regions SKP of the candidate perfusion defect regions MKP of the mixed image data set MB.

Conversely, the method described in FIG. 3 can naturally also be carried out in a similar way such that the automatic detection of the candidate perfusion defect regions is carried out only in the contrast medium image data set, since in this way, the candidate perfusion defect regions found in the contrast medium image data set are segmented and the segmented regions are overlaid on the mixed image data set in step 2.VII. This leads, finally, to the same result.

Therefore, with the method according to an embodiment of the invention, with only a slight extra effort and without additional measurements, the correct detection of perfusion defects, particularly in the myocardium, can be substantially improved, so that based thereon, a better diagnosis and, in particular, a correct treatment plan can be realized.

Finally, it should be noted that the foregoing description of the method and the devices concerns only preferred example embodiments of the invention and that embodiments of the invention can be varied by a person skilled in the art without departing from the scope of the invention as disclosed by the claims. For example, in the method sequences described above, method steps which are given as to be performed in parallel, may possibly also be performed in another order, one after the other. It is also noted that, in place of the mixed image data set, solely the high-energy image data set or the low-energy image data set can also essentially be used. For the sake of completeness, it should also be noted that the use of the indefinite article "a" or "an" does not exclude the possibility that the features concerned can also be plurally present. The expression "unit" also does not exclude the possibility that the item consists of a plurality of components which may possibly also be spatially distributed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the identification of potential perfusion defects in a tissue region through which blood flows in an object under investigation, based on at least one high-energy image data set covering the tissue region and at least one low-energy image data set covering the tissue region, the method comprising:
    establishing a virtual contrast medium image data set based on the at least one high-energy image data set and the at least one low-energy image data set;
    detecting first candidate perfusion defect regions within the virtual contrast medium image data set;
    detecting second candidate perfusion defect regions within a further image data set based on the at least one high-energy image data set and the at least one low-energy image data set; and
    comparing the first candidate perfusion defect regions with the second candidate perfusion defect regions and identifying potential perfusion defects based on the comparing.

2. The method of claim 1, wherein a partial region of the tissue region is only identified as a potential perfusion defect if said partial region is detected as a first candidate perfusion defect region in the virtual contrast medium image data set and as a second candidate perfusion defect region in the further image data set.

3. The method of claim 2, wherein the detection of the first candidate perfusion defect regions within the virtual contrast medium image data set and the detection of the second candidate perfusion defect regions within the further image data set take place independently of one another.

4. The method of claim 3, wherein at least one of the detection of the first candidate perfusion defect regions within the virtual contrast medium image data set and the detection of the second candidate perfusion defect regions within the further image data set takes place automatically.

5. The method of claim 2, wherein at least one of the detection of the first candidate perfusion defect regions within the virtual contrast medium image data set and the detection of the second candidate perfusion defect regions within the further image data set takes place automatically.

6. The method of claim 1, wherein the detection of the first candidate perfusion defect regions within the virtual contrast medium image data set and the detection of the second candidate perfusion defect regions within the further image data set take place independently of one another.

7. The method of claim 6, wherein at least one of the detection of the first candidate perfusion defect regions within the virtual contrast medium image data set and the detection of the second candidate perfusion defect regions within the further image data set takes place automatically.

8. The method of claim 1, wherein at least one of the detection of the first candidate perfusion defect regions within the virtual contrast medium image data set and the detection of the second candidate perfusion defect regions within the further image data set takes place automatically.

9. The method of claim 1, wherein, for identification of image points which is attributable to a potential perfusion defect, a threshold value analysis is carried out.

10. The method of claim 1, wherein at least one of a detected first candidate perfusion defect region and a detected second candidate perfusion defect region are segmented.

11. The method of claim 1, wherein the image data of the virtual contrast medium image data set and corresponding image data of the further image data set are output simultaneously to a display device.

12. The method of claim 11, wherein on overlaid output, at least one of already detected first candidate perfusion defect regions and already detected second candidate perfusion defect regions are marked.

13. The method of claim 11, wherein the image data of the virtual contrast medium image data set and corresponding image data of the further image data set are overlaid on one another.

14. The method of claim 1, wherein the defined tissue region comprises a myocardial tissue.

15. The method of claim 1, wherein initially at least one high-energy image data set of the tissue region of the object under investigation and at least one low-energy image data set of the tissue region or the object under investigation are recorded by way of X-ray measurements with different X-ray energies.

16. A non-transitory computer readable medium, loadable directly into a memory unit of an image analysis apparatus, comprising program code sections which, when executed in the image analysis apparatus, carry out the method of claim 1.

17. A non-transitory computer readable medium including program segments for, when executed on a computer device, causing the computer device to implement the method of claim 1.

18. An image analysis apparatus for identifying potential perfusion defects in a tissue region through which blood flows in an object under investigation, comprising:
  a processor, the processor being configured to form
    an image data set interface, configured to read in, from a memory, at least one high-energy image data set covering the tissue region of the object under investigation and at least one low-energy image data set covering the tissue region of the object under investigation, the at least one high-energy image data set covering a tissue region of the object under investigation and the at least one low-energy image data set covering the tissue region of the object under investigation being generated by a reconstruction unit and the memory storing the generated at least one high-energy image data set and at least one low-energy image data set;
  a contrast medium image determination unit, designed to determine a virtual contrast medium image data set based on the at least one high-energy image data set and the at least one low-energy image data set; and
  a perfusion defect identification unit, designed to
    detect first candidate perfusion defect regions within the virtual contrast medium image data set,
    detect second candidate perfusion defect regions within a further image data set based on at least one of the at least one high-energy image data set and the at least one low-energy image data set, and
    identify potential perfusion defects, based on a comparison of the first candidate perfusion defect regions with the second candidate perfusion defect regions.

19. The image analysis apparatus of claim 18, further comprising:
  the reconstruction unit, configured to generate at least one high-energy image data set covering a tissue region of the object under investigation and the at least one low-energy image data set covering the tissue region of the object under investigation.

20. A computed tomography system comprising:
a scanner;
a detector; and
the image analysis apparatus of claim 19.

21. A computed tomography system comprising;
a scanner;
a detector; and
the image analysis apparatus of claim 18.

* * * * *